(12) United States Patent
Jeanne et al.

(10) Patent No.: US 11,877,827 B2
(45) Date of Patent: Jan. 23, 2024

(54) METHOD AND SYSTEM TO ASSESS TEETH SHADE IN AN UNCONTROLLED ENVIRONMENT

(71) Applicant: KONINKLIJKE PHILIPS N.V., Eindhoven (NL)

(72) Inventors: Vincent Jeanne, Migne Auxances (FR); Taylor Bevis, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 773 days.

(21) Appl. No.: 16/982,863

(22) PCT Filed: Mar. 25, 2019

(86) PCT No.: PCT/EP2019/057358
§ 371 (c)(1),
(2) Date: Sep. 21, 2020

(87) PCT Pub. No.: WO2019/185501
PCT Pub. Date: Oct. 3, 2019

(65) Prior Publication Data
US 2021/0052162 A1     Feb. 25, 2021

Related U.S. Application Data

(60) Provisional application No. 62/649,247, filed on Mar. 28, 2018.

(51) Int. Cl.
*A61C 13/08* (2006.01)
*A61B 5/00* (2006.01)
*A61B 1/24* (2006.01)

(52) U.S. Cl.
CPC .............. *A61B 5/0088* (2013.01); *A61B 1/24* (2013.01); *A61B 5/0013* (2013.01); *A61B 5/6898* (2013.01); *A61B 5/742* (2013.01)

(58) Field of Classification Search
CPC ..... A61C 9/0053; A61C 9/006; A61C 13/082; A61B 5/0088; A61B 5/0013; A61B 5/6898; A61B 5/742; A61B 1/24
(Continued)

(56) References Cited

U.S. PATENT DOCUMENTS 9,478,043 B2 * 10/2016 Abdulwaheed ...... A61B 5/0088
11,744,450 B2 * 9/2023 Chang .................... G03B 15/03
433/29
(Continued)

FOREIGN PATENT DOCUMENTS

JP      2009271093 A    11/2009
RU      2290857 C1      1/2007
(Continued)

OTHER PUBLICATIONS

International Search Report dated Jun. 26, 2019.
http://www.vision.caltech.edu/html-files/EE148-2005-Spring/pprs/viola04ijcv.pdf.
http://www.ri.cmu.edu/pub_files/2013/5/main.pdf.

*Primary Examiner* — Matthew M Nelson

(57) ABSTRACT

A method (300) for characterizing color information about a tooth, comprising: (i) projecting (320) at least one predetermined color pattern (400); (ii) obtaining (330), using an imager (10), one or more images (90) each containing both a projected first predetermined color pattern (400) and at least a portion of a user's mouth (500); (iii) automatically identifying (340) by a controller (30), from the obtained one or more images, one or more teeth (510) in the at least a portion of the user's mouth (500( ); (iv) comparing (350) an imaged predetermined color pattern to a corresponding projected predetermined color pattern; and (v) extracting (360) by the controller, based on the outcome of the comparison, color information about the one or more identified teeth (510).

14 Claims, 4 Drawing Sheets

(58) Field of Classification Search
USPC .......................................................... 433/29
See application file for complete search history.

(56) References Cited

U.S. PATENT DOCUMENTS

| | | | | |
|---|---|---|---|---|
| 2009/0067695 | A1* | 3/2009 | Komiya | G01J 3/0272 |
| | | | | 348/222.1 |
| 2010/0303315 | A1* | 12/2010 | Rohner | G01J 3/02 |
| | | | | 382/128 |
| 2013/0244197 | A1* | 9/2013 | Tjioe | G01J 3/0264 |
| | | | | 433/29 |
| 2017/0165038 | A1* | 6/2017 | Esbech | A61C 13/082 |
| 2020/0205942 | A1* | 7/2020 | Pesach | G06T 7/579 |
| 2020/0288981 | A1* | 9/2020 | Li | G01B 11/2518 |
| 2021/0052162 | A1* | 2/2021 | Jeanne | A61B 5/6898 |
| 2023/0233295 | A1* | 7/2023 | Li | A61B 5/0088 |
| | | | | 348/66 |

FOREIGN PATENT DOCUMENTS

| | | | |
|---|---|---|---|
| WO | 2015082300 | A1 | 6/2015 |
| WO | 2017046829 | A1 | 3/2017 |

* cited by examiner

METHOD AND SYSTEM TO ASSESS TEETH SHADE IN AN UNCONTROLLED ENVIRONMENT

This application is the U.S. National Phase application under 35 U.S.C. § 371 of International Application No. PCT/EP2019/057358, filed on Mar. 25, 2019, which claims the benefit of U.S. Provisional Application Ser. No. 62/649,247, filed Mar. 28, 2018. These applications are hereby incorporated by reference herein.

FIELD OF THE INVENTION

The present disclosure is directed generally to methods and systems for characterizing color information about a user's teeth.

BACKGROUND

Tooth discoloration is an issue of concern for many individuals. A consumer's aesthetic requirements regarding the treatment of teeth discoloration is mainly focused on the restoration of a natural color of the teeth. Indeed, dental shade is one of the most important aesthetic components of dental care among adults and is often addressed by whitening procedures or treatments. Assessment of tooth color or shade is most commonly performed by dental professional using dedicated tools. However, with the advent of so many different smart and connected devices, consumers are increasingly turning to their own devices to perform tasks typically performed by professionals, including assessing tooth color or shade.

As with any color measurement the determination of teeth color or shade is significantly affected by the environment. Many factors affect the perception of an object's color, including but not limited to the lighting conditions and/or the reflectance of the object. One common technique to overcome the challenge of tooth color determination is to utilize so-called calibration patterns, which are dedicated objects comprising or displaying one or more known colors. While calibration patterns are effective under homogeneous lighting, they are relatively ineffective under challenging lighting environments such as those containing an illumination gradient (e.g. shadows and/or multiple light sources). Additionally, although there are methods that assist a consumer with determining tooth color or shade, these methods place a significant burden on the consumer as they must first calibrate the system and then utilize a separate or dedicated imaging device to capture and/or assess the tooth color or shade. This can be both time-consuming and expensive for the consumer, which minimizes any benefit gained by at-home tooth color characterization.

Accordingly, there is a continued need in the art for simple and effective methods and systems that allow users to accurately characterize the color or shade of their teeth.

SUMMARY OF THE INVENTION

The present disclosure is directed to inventive methods and systems for characterizing color information about a user's teeth. Various embodiments and implementations herein are directed to a system configured to obtain and analyze images of a user's mouth. The system projects a predetermined color pattern on a screen and obtains one or more images that contain both the predetermined color pattern and a portion of the user's mouth. The system automatically identifies, using the images, one or more teeth in the imaged portion of the user's mouth. The system then compares the imaged color pattern to the projected predetermined color pattern, and extracts, based on the outcome of the comparison, color information about the one or more identified teeth. The system can optionally transmit that color information to a dental professional.

Generally, in one aspect, a method for characterizing color information about a tooth is provided. The method includes: (i) projecting at least one predetermined color pattern; (ii) obtaining, using an imager, one or more images each containing both a projected predetermined color pattern and at least a portion of a user's mouth; (iii) automatically identifying by a controller, from the obtained one or more images, one or more teeth in the at least a portion of the user's mouth; and (iv) comparing an imaged color pattern to a corresponding projected predetermined color pattern; and (v) extracting by the controller, based on the outcome of the comparison, color information about the one or more identified teeth.

According to an embodiment, the predetermined color pattern comprises a single color.

According to an embodiment, the method further includes the step of transmitting the obtained one or more images to a remote server.

According to an embodiment, the method further includes the step of transmitting the extracted color information to a dental professional.

According to an embodiment, the method further includes the step of selecting, based on the outcome of the comparison and/or on the extracted color information, a second predetermined color pattern to project.

According to an embodiment, the imager is a component of a smartphone.

According to an embodiment, projecting the predetermined color pattern comprises displaying the color pattern on a screen. According to an embodiment, projecting the predetermined color pattern comprises projecting the color pattern on a surface.

According to another aspect is a device for characterizing color information about a tooth. The device includes: a display or projector configured to display or project at least one predetermined color pattern; an imager configured to obtain one or more images each containing both a projected predetermined color pattern and at least a portion of a user's mouth; and a controller configured to: (i) identify, from the obtained one or more images, one or more teeth in the at least a portion of the user's mouth; (ii) compare an imaged predetermined color pattern to a corresponding projected predetermined color pattern; and (iii) extract, based on the outcome of the comparison, color information about the one or more identified teeth.

According to an embodiment, the device further comprises a communications module configured to transmit one or more images and/or extracted color information about the one or more identified teeth.

According to another aspect is a system for characterizing color information about a tooth. The system includes an imaging device comprising: (i) a display or projector configured to display or project at least one predetermined color pattern; and (ii) an imager configured to obtain one or more images each containing both a projected predetermined color pattern and at least a portion of a user's mouth; and further includes a controller configured to: (i) identify, from the obtained one or more images, one or more teeth in the at least a portion of the user's mouth; (ii) compare an imaged predetermined color pattern to a corresponding projected predetermined color pattern; and (iii) extract, based on the outcome of the comparison, color information about the one or more identified teeth.

As used herein for purposes of the present disclosure, the term "controller" is used generally to describe various apparatus relating to the operation of an imaging apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The disclosure describes various embodiments of a method and device for tooth imaging. More generally, Applicant has recognized and appreciated that it would be beneficial to provide an easy-to-use automated system to characterize color information about teeth from obtained images. Accordingly, the methods described or otherwise envisioned herein provide an imaging device or system such as a smartphone, smart mirror, and/or other imaging device configured to obtain one or more images of the individual's dental region. The imaging device or system simultaneously displays a predetermined color pattern on a screen and obtains one or more images that contain both the predetermined color pattern and a portion of the individual's dental region. The system automatically identifies, using the images, one or more teeth in the imaged portion of the user's mouth. The system then compares the imaged color pattern to the projected predetermined color pattern, and extracts, based on the outcome of the comparison, color information about the one or more identified teeth. The system can optionally transmit that color information to a dental professional where it can be utilized for analysis by the professional.

Figure 1:
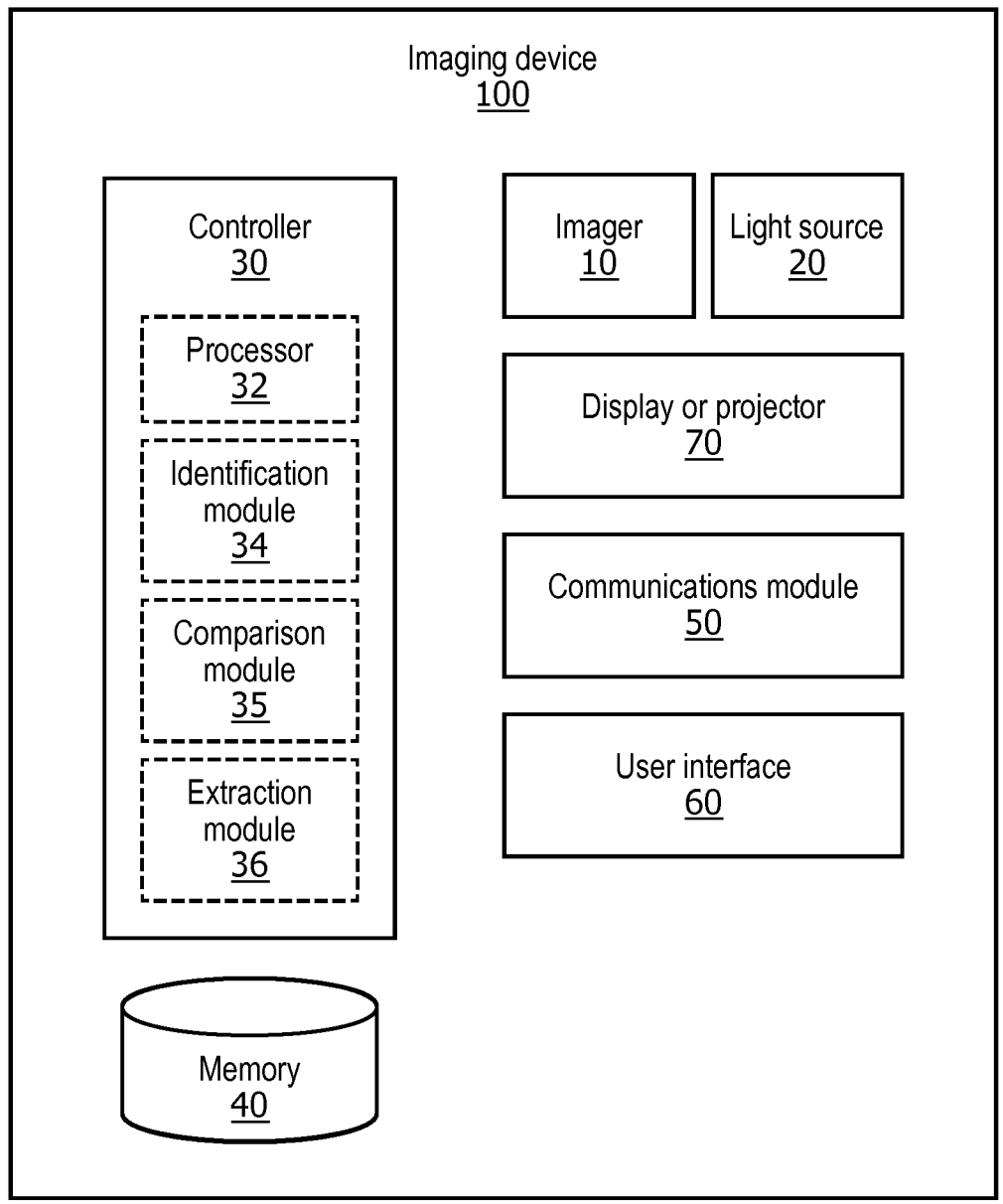
FIG. 1 is a schematic representation of an imaging device, in accordance with an embodiment.

Referring to FIG. 1, in one embodiment, is an imaging device 100 configured to obtain one or more images of an individual's dental region. Imaging device 100 may be any device with an imager capable of obtaining images of an individual's dental region in a digital format. For example, imaging device 100 may be a smartphone, smart mirror, wearable computing device, digital camera, laptop, and/or any other computing device or capture device capable of capturing images. The imaging device 100 may optionally comprise software such as an application which facilitates one or more aspects of the imaging system or method as described or otherwise envisioned herein.

Imaging device 100 comprises an imager 10 configured to obtain images of an individual's dental region. Imager 10 is an image sensor such as a CCD or CMOS sensor, among others. For example, imager 10 may be a standalone digital camera, or may be a camera integrated into an oral care device, a smartphone, a smart mirror, a wearable device, and/or any other computing or image capture device. The imaging device 100 or imager 10 may comprise or otherwise be in communication with a light source 20 configured to illuminate one or more regions of the mouth. For example, light source 20 may be a flash or other light source associated with the device or system. Light source 20 can be or comprise any light source, such as an LED light source, that emits light capable of facilitating high-quality oral imaging. According to an embodiment, the light source comprises light from two or more light sources. The imager 10 and/or light source 20 may be configured to operate periodically, continuously, and/or in response to a stimulus. For example, the imager 10 and light source 20 can obtain an image in response to a user taking an image, or in response to a user positioning the imager over a portion of the oral cavity, as detected by the imager in real-time.

Imaging device 100 further comprises a controller 30 configured to receive the one or more images obtained from the imager 10. Controller 30 may be formed of one or multiple modules, and can configured to operate the imager 10 in response to an input, such as input obtained via a user interface. Controller 30 can comprise, for example, at least a processor 32. The processor 32 may take any suitable form, including but not limited to a microcontroller, multiple microcontrollers, circuitry, a single processor, or plural processors. Controller 30 and/or imaging device 100 may also comprise a memory 40. The memory 40 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of imaging device 100.

Imaging device 100 further comprises a communications module 50 configured to receive and/or transmit information via a wired and/or wireless communications network. The communications module 50 can be any module, device, or means capable of transmitting a wired or wireless signal, including but not limited to a Wi-Fi, Bluetooth, near field communication, and/or cellular module. The communications module 50 can, for example, transmit one or more images obtained by the imager, and/or color information about one or more of the user's teeth.

According to an embodiment, imaging device 100 includes a user interface 60 configured to provide information to a user and/or receive information from a user. The user interface 60 can take many different forms, but is configured to provide information to the user and/or receive information from the user. For example, the information can be read, viewed, heard, felt, and/or otherwise interpreted. Accordingly, the user interface may be a display that provides information to the user, a haptic mechanism that provides haptic feedback to the user, a speaker to provide sounds or words to the user, a simple LED light or array of LEDS, or any of a variety of other user interface mechanisms. According to an embodiment, the user interface 60 provides feedback to a user as images are obtained or after images are obtained. User interface 60 can also provide instructions or guidance to the user about images to obtain, or about improving images, among many other types of information and guidance.

Imaging device 100 further comprises a display or projector 70. Display 70 may be a screen or other display configured to display one or more color patterns as described or otherwise envisioned herein. Projector 70 may be a projector or other image display configured to project a color pattern on a surface as described or otherwise envisioned herein.

Figure 2:
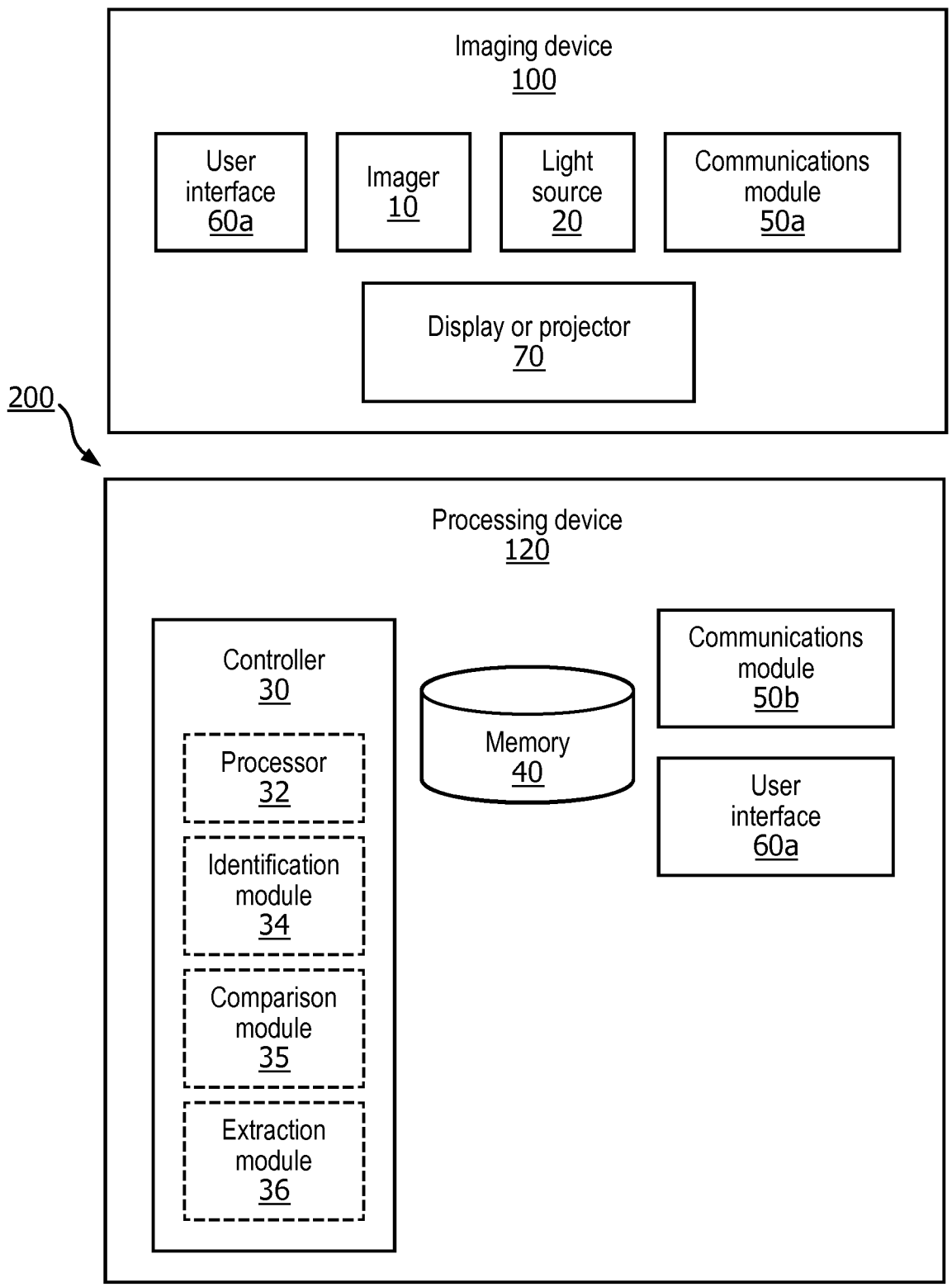
FIG. 2 is a schematic representation of an imaging system, in accordance with an embodiment.

Referring to FIG. 2, in one embodiment, is an imaging system 200 configured to obtain images of an individual's dental region. According to this embodiment, imaging system 200 comprises an imaging device 100 and a processing device 120. Imaging device 100 is configured to obtain one or more images of the user's mouth, and to transmit those images to the processing device 120 which may be locally or remotely located, or even be part of the imaging device 100. For example, imaging device 100 may be co-located with a user, while processing device 120 may be located remotely from the user, such as with a dental professional or with a cloud-based implementation. Many other configurations are possible. Processing device 120 is configured to receive and analyze the one or more images received from the imaging device to extract color information about the user's teeth.

Imaging device 100 can be any device with an imager capable of obtaining images of an individual's dental region, preferably in a digital format. For example, imaging device 100 may be a smartphone, smart mirror, wearable computing device, digital camera, laptop, and/or any other computing device or capture device capable of capturing images. The imaging device 100 may optionally comprise software such as an application which facilitates one or more aspects of the imaging system or method as described or otherwise envisioned herein. Imaging device 100 comprises an imager 10, such as a CCD or CMOS sensor, among others, configured to obtain images from a user's mouth. Imaging device 100 may be a standalone digital camera, or may be a camera integrated into an oral care device, a smartphone, a smart mirror, a wearable device, and/or any other computing device. Imaging device 100 may comprise a light source 20 configured to illuminate one or more regions of the mouth.

Imaging device 100 also comprises a communications module 50a configured to receive and/or transmit information via a wired and/or wireless communications network. The communications module 50a can be any module, device, or means capable of transmitting a wired or wireless signal, including but not limited to a Wi-Fi, Bluetooth, near field communication, and/or cellular module. The communications module 50a can, for example, transmit one or more images obtained by the imager to the processing device 120.

According to an embodiment, imaging device 100 also includes a user interface 60a, such as user interface 60 as described previously herein, configured to provide information to a user and/or receive information from a user. The user interface 60a can take many different forms, and is configured to provide information to the user and/or receive information from the user. According to an embodiment, the user interface 60a provides feedback to a user as images are obtained or after images are obtained. User interface 60a can also provide instructions or guidance to the user about images to obtain, or about improving imaging, among many other types of information and guidance.

Processing device 120 can be any device configured to receive images from the imaging device 100. For example, processing device 120 may be a smartphone, smart mirror, computer, laptop, server, and/or any other computing device. Processing device 120 may optionally comprise software such as an application which facilitates one or more aspects of the imaging system or method as described or otherwise envisioned herein.

Processing device 120 comprises a controller 30 configured to receive the one or more images obtained from the imager. Controller 30 may be formed of one or multiple modules, and can comprise, for example, processor 32. The processor 32 may take any suitable form, including but not limited to a microcontroller, multiple microcontrollers, circuitry, a single processor, or plural processors. Processing device 120 may comprise a memory 40, which can take any suitable form, including a non-volatile memory and/or RAM. The memory 40 can be configured to store one or more received images or any other information or instructions.

The processing device further comprises a communications module 50b configured to receive and/or transmit information via a wired and/or wireless communications network, including information transmitted from communications module 50a of the imaging device 100. The communications module 50b can be any module, device, or means capable of transmitting a wired or wireless signal, including but not limited to a Wi-Fi, Bluetooth, near field communication, and/or cellular module.

According to an embodiment, processing device 120 includes a user interface 60b configured to provide information to a user and/or receive information from a user. The user interface 60b can take many different forms, and is configured to provide information to the user and/or receive information from the user. According to an embodiment, the user interface 60b provides feedback to a user as images are obtained or after images are obtained. User interface 60b can also provide instructions or guidance to the user about images to obtain, or about improving imaging, among many other types of information and guidance.

Figure 3:
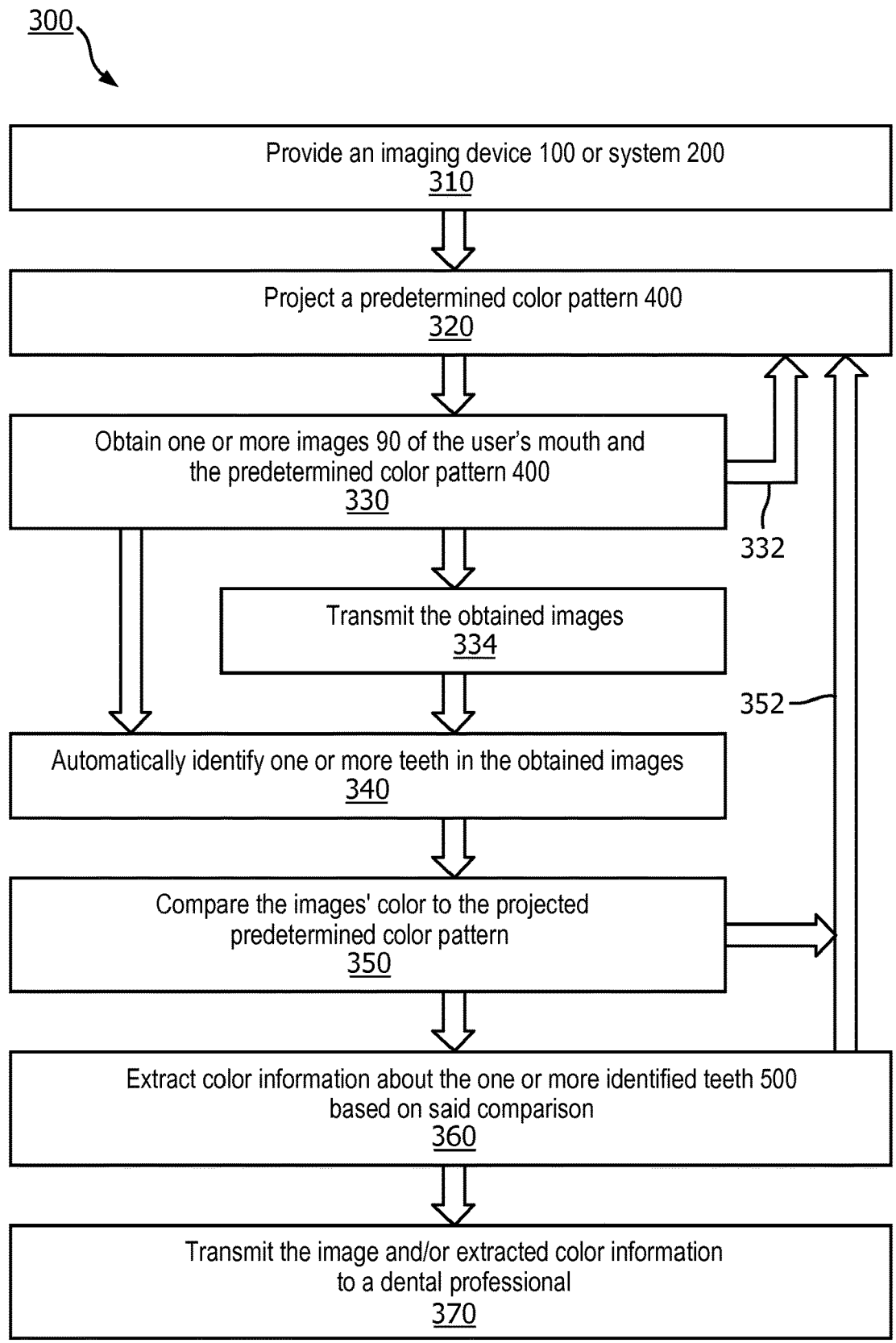
FIG. 3 is a flowchart of a method for characterizing color information about a user's teeth, in accordance with an embodiment.

Referring to FIG. 3, in one embodiment, is a flowchart of a method 300 for characterizing color information about a tooth. At step 310, a tooth color characterization device or system is provided. The tooth color characterization device or system may be any of the devices or systems described or otherwise envisioned herein. For example, the tooth color characterization device or system may be device 100 or system 200, among many other devices or systems. Generally, the tooth color characterization device or system will comprise an imager 10 configured to obtain one or more images of a user's mouth, a controller 30 configured to receive and analyze the obtained one or more images, a communications module 50 configured to transmit and/or receive information over a wired and/or wireless communications system, and a user interface 60 to receive information from a user and/or provide information to a user. Although method 300 is described within the framework of device 100 and system 200, the method can be implemented using any other appropriately configured tooth color characterization device or system as described or otherwise envisioned herein.

At step 320 of the method, the device or system projects one or more predetermined color patterns 400. The color pattern can be projected or displayed using any mechanism for projection or display. According to an embodiment, the user positions in front of a mirror and the predetermined color pattern is displayed on the screen of a device held up to be seen in the mirror, and/or the mirror itself displays the predetermined color pattern. According to another embodiment, the device 100 or system 200 comprises a projector and projects one or more color patterns 400 onto a surface. The projected color pattern 400 comprises a set of predetermined colors expected to depict achievable teeth shades. Additionally, or alternatively, multiple versions of a predetermined color pattern 400 are generated to include different illumination gradient properties and angles.

Figure 5:
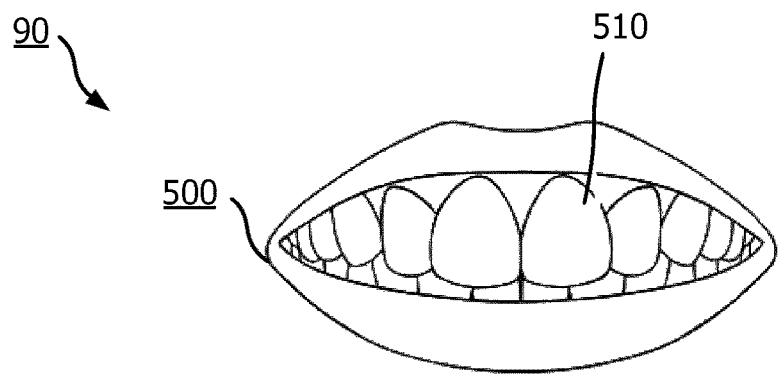
FIG. 5 is a representation of an image of a user's teeth, in accordance with an embodiment.

According to an embodiment, the device 100 or system 200 comprises a driver ensuring that the one or more color patterns are projected at the same time an image 90 of at least a portion of the person's teeth, such as shown in FIG. 5, is acquired, and to ensure that the imager 10 has sufficient time to capture both the projected pattern(s) 400 and an image 90 of at least a portion of the user's mouth in view of the imager properties, including but not limited to shutter time, aperture, exposure, white/balance, and other settings, properties, and parameters.

Figure 4:
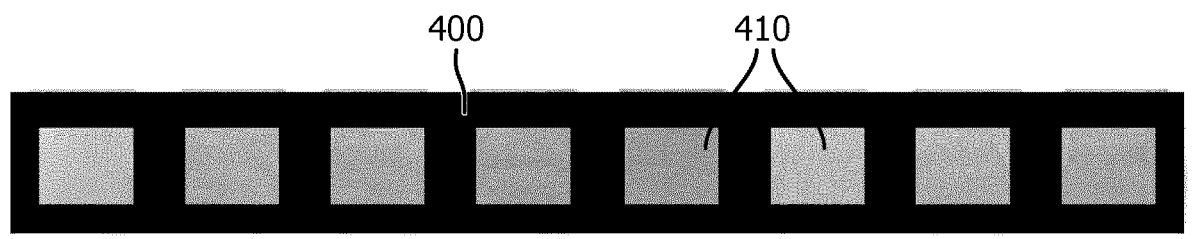
FIG. 4 is a representation of a color pattern for display or projection, in accordance with an embodiment.

Referring to FIG. 4, in one embodiment, is a representation of a predetermined color pattern 400. Although an example of a predetermined color pattern is shown in FIG. 4, it is only an example and thus many other patterns and formats are possible. Each of the color squares 410 comprises a different color, which may be a specific or variable difference from a neighboring square, as long as the specific color of each square is known by the system. In addition to the color squares shown in FIG. 4, the predetermined color pattern may comprise circles, a spectrum ranging from one wavelength to another, and/or many other shapes, sizes, patterns, and configurations.

At step 330 of the method, the imager 10 of the device 100 or system 200 obtains one or more images 90 of at least a portion of a user's mouth 500, as shown in FIG. 5, and the projected or displayed one or more predetermined color patterns 400. In an embodiment, the user's mouth 500 is in proximity in the image to the one or more predetermined color patterns. According to an embodiment the imager is a 2D imaging sensor integrated into a smart connected medium such as a smartphone, laptop, or other connected camera that enables the capture of wavelengths in the visible part of the spectrum.

According to an embodiment, image capture comprises capturing one or multiple images. For example, the system may obtain a series of images to allow the user to automatically select a best image according, and/or to allow the system or a dental professional to select the most appropriate image or images from the series for analysis.

The device or system may provide instructions or directions to the user about image capture. The device or system may provide feedback to the user about the images 90 that are obtained, to obtain the best possible images. For example, the user may be prompted to obtain images at a specific angle, or to include certain teeth in the field of view, among many other possible prompts.

The images obtained by the user via the imager may be of any portion of the user's mouth, including but not limited to gums, teeth, tongue, or any other part of the oral cavity. The images may be analyzed immediately or may be stored for batch processing in real-time or near real-time. The images may be retained by the device for analysis or may be transmitted to another device for downstream analysis as described or otherwise envisioned herein. According to an embodiment, the images are transmitted to and/or received by controller 30 for feature extraction and analysis.

At optional step 332 of the method, the device 100 or system 200 projects or displays a different predetermined color pattern 400, and at step 330 the device or system captures an additional one or more images 90 of the user's mouth 500 and the projected or displayed different predetermined color pattern. This allows a variety of color patterns each with a variety of colors to be displayed and captured. Obtaining multiple color patterns can occur in response to user selections or stimulus or can happen automatically. For example, the device or system may be programmed or configured to obtain images for a variety of color patterns, which can be performed in rapid succession and/or with a predetermined time between each color pattern.

At optional step 334 of the method, the device or system transmits the obtained images 90. The images may be transmitted to another device which is locally or remotely located. For example, the images may be obtained by a smartphone or smart mirror among many other imaging devices, and can be transmitted to a laptop, computer, or other device for analysis. The images may additionally or alternatively be transmitted to a cloud-based server or service, and/or to a dental professional, or analysis according to the methods described or otherwise envisioned herein.

At step 340 of the method, the device or system automatically identifies one or more teeth 500 from the user's mouth in the obtained images 90. This facilitates extraction of color information about these identified teeth. According to an embodiment, the imaging device or system comprises an Identification Module 34 which is configured to analyze the one or more images 90 to identify teeth 510 from the user's mouth 500. The system may utilize a face detection algorithm or classifier, and/or a facial feature detection algorithm or classifier. The system may utilize three-dimensional information and shape matching, and/or template matching, to identify teeth from the user's mouth. According to an embodiment, the system may align the device 100 manually to fit his/her face on an overlay superimposed on the camera image, among many other options.

According to an embodiment, Identification Module 34 extracts one or more features from the obtained one or more images 90. Once extracted, the one or more features can be analyzed in real-time or near real-time or can be stored for subsequent analysis. For example, the extracted one or more features can be stored in memory 40 and extracted features can be associated in memory with the image or images from which they were obtained.

According to an embodiment, the system is configured to determine what hardware is being utilized to display the color patterns and/or to obtain the images. For example, the system may project a predetermined shape on the device screen and detect it by means of machine learning algorithms such as a trained classifier, project a specific sequence of light color and/or intensity, or comprise an algorithm configured to detect the shape of the device by means of a trained classifier or low levels features such as a Hough transform, among many other methods. According to an embodiment, the system may be configured to detect the screen using the dimension properties of the device and device orientation. The system can be configured to track or otherwise record the determined hardware information and apply it on each sub-sequent loop in this process to limit the search space of these objects, thereby reducing computation load on the system.

At step 350 of the method, the device or system compares the color pattern of the image 90 to the projected predetermined color pattern 400. This enables the device or system to detect the effect of the environment and/or imaging device or software on the projected predetermined color pattern 400, and enables the device or system to account for those effects when calculating the color of the identified teeth 510. According to an embodiment, the device or system comprises a Comparison Module 35 which is programmed or configured to analyze the images to identify color differences between a projected predetermined color pattern and an image of that same projected predetermined color pattern obtained by the device or system. Comparison Module 35 may compare a portion of the imaged and projected color patterns, or may compare the entire imaged and projected color patterns. Comparison Module 35 can calculate—including but not limited to pixel by pixel, using an average, or using any other method—the difference between at least a portion of the imaged and projected color patterns. The difference may be represented by a number, a color difference, an adjustment factor, or any other representation which is sufficient to be utilized by the device or system.

At step 360 of the method, the device or system extracts color information about the one or more identified teeth 510 using the outcome of the comparison from step 350 of the method. According to an embodiment, the device or system comprises an Extraction Module 36 which is programmed or configured to utilize the outcome of the comparison of the of the imaged and projected color patterns to analyze the images and characterize color information about the one or more identified teeth. For example, Extraction Module 36 may receive from the Comparison Module 35 the outcome of the comparison of the of the imaged and projected color patterns. This may be an adjustment factor or any other representation of the comparison, which represents the effects of the environment and/or imager on the color of the teeth 510 as described herein. The Extraction Module utilizes this representation to extract and properly adjust color characteristics from the detected regions of interest in the image(s), namely the user's mouth or teeth. In a preferred embodiment color extraction is performed on the original image providing color information on the RGB (red, green, blue) color channel. In other embodiments, the color extraction can be performed on in either YUV, LAB or HSV color space. Many other systems and methods may be utilized to extract color information about the one or more identified teeth using the one or more predetermined color patterns captured in the image(s). According to an embodiment, the device or system stores the extracted color characteristics of each region of interest in memory.

According to an embodiment, the device or system calculates a distance between the color characteristics extracted from the regions of interest, namely the user's mouth or teeth and the device screen comprising the one or more predetermined color patterns. For example, the distance may be calculated along each dimension of the used color space using Euclidian distance.

According to an embodiment, at optional step 352 of the method, the device or system modifies the sequence, selection, and/or number of projected color patterns 400 based on this determined color distance. In a practical embodiment, rather than projecting the next pattern available in the system the system will favor a pattern that minimizes the previously calculated distance along at least one dimension of the color space. This minimization may be performed by brute-force search or by solving a minimization equation. According to an embodiment, the device or system modifies or otherwise adapts the sequence, selection, and/or number of projected predetermined color patterns after comparing the imaged color pattern to the projected predetermined color pattern, and/or after extracting color information about the one or more identified teeth based on said comparison. For example, the system or device may adjust or select the next predetermined color pattern to be projected based on a determined color difference, which informs the system or device about the environment affecting the color imaging. As another example, the system or device may adjust or select the next predetermined color pattern to be projected based on a color of the user's teeth extracted by the device or system. The system selects the next predetermined color pattern to be projected after determining that, based on a color extracted from the user's teeth, the true color of the teeth can be better characterized using a particular predetermined color pattern.

According to an embodiment, once the system has looped through all available color patterns or when distance minimization criteria are met, all extracted color characteristics of the screen are used to define the mapping between the real color space, namely color characteristics corresponding to the true value of the projected patterns, and the perceived color space. In a preferred embodiment, the mapping is performed by assuming either a linear or a non-linear transformation between both real and perceived spaces. The system may define the transformation matrix minimizing the projection error across all measurement, for example.

According to an embodiment, once the mapping/transformation is computed, the mouth color exhibiting the smallest distance with its respective projected pattern is projected in the real color space to compute the true color of the user's teeth 510. This information can be shared with the user, such as via a digital medium, and can be used: (1) for direct metric feedback; (2) for comparison against previously measured shades to provide longitudinal feedback; (3) to send to a third-party system to support an either future or on-going dental treatment.

At optional step 370 of the method, the system or device transmits the image(s) and/or extracted color information to a dental professional. Images can be transmitted to the dental professional or other third-party system or service via wired and/or wireless communication using a communications module 50 of the imaging device or system. The system may be configured or designed to only transmit images 90 to a dental professional or other third-party system or service if one or more predetermined criterion is met and/or if color information is successfully captured. The system may be configured or designed to transmit images 90 to a dental professional or other third-party system or service in response to a command from the user and/or in response to a request from the dental professional or other third-party system or service.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for characterizing color information about a tooth, comprising:
    projecting at least one predetermined color pattern;
    obtaining using an imager, one or more images each containing both a projected predetermined color pattern and at least a portion of a user's mouth;
    automatically identifying by a controller, from the obtained one or more images, one or more teeth in the at least a portion of the user's mouth;
    comparing an imaged predetermined color pattern to a corresponding projected predetermined color pattern; and
    extracting by the controller, based on the outcome of the comparison, color information about the one or more identified teeth.

2. The method of claim 1, wherein the predetermined color pattern comprises a single color.

3. The method of claim 1, further comprising the step of transmitting the obtained one or more images to a remote server.

4. The method of claim 1, further comprising the step of transmitting the extracted color information to a dental professional.

5. The method of claim 1, further comprising the step of selecting based on the outcome of the comparison and/or on the extracted color information, a second predetermined color pattern to project.

6. The method of claim 1, wherein the imager is a component of a smartphone.

7. The method of claim 1, wherein projecting the predetermined color pattern comprises displaying the color pattern on a screen or on a surface.

8. The method of claim 1, wherein the user's mouth is in proximity in the image to the predetermined color pattern.

9. A system for characterizing color information about a tooth, comprising:

an imaging device comprising: (i) a display or projector configured to display or project at least one predetermined color pattern; and (ii) an imager configured to obtain one or more images each containing both a projected predetermined color pattern and at least a portion of a user's mouth; and a controller configured to: (i) identify, from the obtained one or more images one or more teeth in the at least a portion of the user's mouth; (ii) compare an imaged predetermined color pattern to a corresponding projected predetermined color pattern; and (iii) extract, based on the outcome of the comparison, color information about the one or more identified teeth.

10. The system of claim 9, wherein the imaging device is a smartphone.

11. The system of claim 9, further comprising a communications module configured to transmit one or more images and/or extracted color information about the one or more identified teeth.

12. The system of claim 9, wherein, the controller is further configured to select, based on the outcome of the comparison and/or on the extracted color information, a second predetermined color pattern to project.

13. The system of claim 9, wherein the controller is part of the imaging device.

14. The system of claim 13, wherein the system is a smartphone.

* * * * *